(12) United States Patent
Noda

(10) Patent No.: US 11,234,846 B2
(45) Date of Patent: Feb. 1, 2022

(54) GUIDE CATHETER AND DELIVERY SYSTEM

(71) Applicant: OLYMPUS CORPORATION, Hachioji (JP)

(72) Inventor: Kazuhiro Noda, Ebina (JP)

(73) Assignee: OLYMPUS CORPORATION, Tokyo (JP)

( * ) Notice: Subject to any disclaimer, the term of this patent is extended or adjusted under 35 U.S.C. 154(b) by 201 days.

(21) Appl. No.: 16/177,822

(22) Filed: Nov. 1, 2018

(65) Prior Publication Data

US 2019/0070030 A1   Mar. 7, 2019

Related U.S. Application Data

(63) Continuation of application No. PCT/JP2017/020979, filed on Jun. 6, 2017.

(30) Foreign Application Priority Data

Jun. 8, 2016   (JP) .............................. JP2016-114710
Jun. 8, 2016   (JP) .............................. JP2016-114711

(51) Int. Cl.
  *A61F 2/966*   (2013.01)
  *A61M 25/00*   (2006.01)
  *A61M 25/06*   (2006.01)

(52) U.S. Cl.
  CPC ........... *A61F 2/966* (2013.01); *A61M 25/007* (2013.01); *A61M 25/0023* (2013.01);
  (Continued)

(58) Field of Classification Search
  CPC ............ A61F 2/966; A61F 2002/9554; A61M 2025/015; A61M 25/0147
  See application file for complete search history.

(56) References Cited

U.S. PATENT DOCUMENTS

| 4,586,923 A | * | 5/1986 | Gould | ............. | A61M 25/09033 600/434 |
| 4,777,955 A | * | 10/1988 | Brayton | ............... | A61B 1/0058 600/374 |
| 5,042,707 A | * | 8/1991 | Taheri | .................. | A61B 17/115 606/213 |

(Continued)

FOREIGN PATENT DOCUMENTS

| JP | H08-187292 A | 7/1996 |
| JP | 2016-093350 A | 5/2016 |

(Continued)

OTHER PUBLICATIONS

Sep. 12, 2017, International Search Report issued in Patent Application No. PCT/JP2017/020979.

(Continued)

*Primary Examiner* — Alexander J Orkin
(74) *Attorney, Agent, or Firm* — Oliff PLC

(57) ABSTRACT

This guide catheter includes a resin tube having an inner lumen through which a guide wire is insertable; a metal pipe attached to an inside of the tube to be coaxial with the tube; and a metal wire having a distal end portion welded to a region more distal than a proximal end of the pipe on an outer circumferential surface of the pipe. The pipe has a most proximal portion formed in a proximal end surface of the pipe, the most proximal portion is more proximal than other portions of the proximal end surface in a central axis direction of the pipe. A welding region of the wire welded to the pipe is formed on the outer circumferential surface of the pipe and a proximal end of the welding region is positioned apart from the most proximal portion of the pipe in the central axis direction of the pipe.

4 Claims, 12 Drawing Sheets

(52) U.S. Cl.
CPC ............... *A61M 25/0662* (2013.01); *A61F 2250/0021* (2013.01); *A61M 25/0009* (2013.01); *A61M 2025/006* (2013.01)

(56) References Cited

U.S. PATENT DOCUMENTS

| | | | | |
|---|---|---|---|---|
| 5,231,989 | A * | 8/1993 | Middleman | A61M 25/0147 600/434 |
| 6,248,100 | B1 | 6/2001 | de Toledo et al. | |
| 6,544,215 | B1 * | 4/2003 | Bencini | A61M 25/0144 600/585 |
| 6,976,979 | B2 * | 12/2005 | Lawrence | A61M 25/005 604/164.13 |
| 2007/0123971 | A1 * | 5/2007 | Kennedy, II | A61F 2/95 623/1.11 |
| 2008/0188800 | A1 * | 8/2008 | Bencini | A61M 25/0141 604/95.01 |
| 2009/0182268 | A1 * | 7/2009 | Thielen | A61M 25/0138 604/95.04 |
| 2014/0243953 | A1 * | 8/2014 | Stante | A61F 2/2433 623/2.11 |
| 2015/0133857 | A1 * | 5/2015 | Rokde | A61M 25/0147 604/95.04 |
| 2016/0367787 | A1 * | 12/2016 | Van Hoven | A61F 2/246 |
| 2018/0071490 | A1 * | 3/2018 | Khuu | F16H 25/16 |

FOREIGN PATENT DOCUMENTS

| | | |
|---|---|---|
| WO | 2006/113866 A2 | 10/2006 |
| WO | 2013/133081 A1 | 9/2013 |

OTHER PUBLICATIONS

Sep. 24, 2019 Japanese Office Action issued in Japanese Patent Application No. 2016-114711.

* cited by examiner

GUIDE CATHETER AND DELIVERY SYSTEM

This application is a continuation application based on a PCT International Application No. PCT/JP2017/020979, filed on Jun. 6, 2017, whose priority is claimed on a Japanese Patent Application No. 2016-114710 and a Japanese Patent Application No. 2016-114711, both filed on Jun. 8, 2016. Contents of the PCT International Application, and both of the Japanese Patent Applications are incorporated herein with reference.

BACKGROUND OF THE INVENTION

Field of the Invention

The present invention relates to a guide catheter and a delivery system for delivering a stent.

Description of Related Art

Conventionally, a medical device having a guide catheter capable of being combined to use with a guidewire is known.

For example, in U.S. Pat. No. 6,248,100, a stent delivery system having a wire configured to move a tube into which a guidewire can be inserted to a hand side by a handle operation is disclosed. In the stent delivery system according to U.S. Pat. No. 6,248,100, a stent can be placed in a desired position by using a wire to move a tube inserted through by the stent to the hand side.

SUMMARY OF THE INVENTION

According to a first aspect of the present invention, a guide catheter has a tube formed from a resin and having an inner lumen through which a guide wire is insertable; a metal pipe configured to be attached to an inside of the tube so as to be coaxial with the tube; and a metal wire having a distal end portion welded to a region more distal than a proximal end of the pipe on an outer circumferential surface of the pipe, wherein the pipe has a most proximal portion formed in a proximal end surface of the pipe, the most proximal portion is more proximal than other portions of the proximal end surface in a central axis direction of the pipe, and wherein a welding region of the wire welded to the pipe is formed on the outer circumferential surface of the pipe and a proximal end of the welding region is positioned apart from the most proximal portion of the pipe in the central axis direction of the pipe.

According to a second aspect of the present invention, in the guide catheter according to the first aspect, the pipe may include an opposite portion positioned at an opposite side of the most proximal portion in a radial direction of the pipe in the proximal end surface while positioned at a most distal end side in the proximal end surface, and the opposite portion may be positioned more proximally than the welding portion in the central axis direction of the pipe.

According to a third aspect of the present invention, in the guide catheter according to the first aspect, the pipe may include an opposite portion positioned at an opposite side of the most proximal portion in a radial direction of the pipe in the proximal end surface while positioned at a most distal end side in the proximal end surface, and the opposite portion may be positioned more distally than a proximal end of the welding region and apart from a distal end of the pipe toward the proximal end of the pipe.

According to a fourth aspect of the present invention, in the guide catheter according to the first aspect, the proximal end surface of the pipe may be inclined with the central axis of the pipe, and the pipe may include an opposite portion positioned at an opposite side of the most proximal portion in a radial direction of the pipe in the proximal end surface of the pipe while being positioned at a most distal end side in the proximal end surface of the pipe.

According to a fifth aspect of the present invention, in the guide catheter according to the second aspect, the opposite portion and the outer circumferential surface of the pipe may be connected at an obtuse angle or with a curved surface.

According to a sixth aspect of the present invention, in the guide catheter according to the third aspect, the opposite portion and the outer circumferential surface of the pipe may be connected at an obtuse angle or with a curved surface.

According to a seventh aspect of the present invention, a guide catheter includes a tube formed from a resin and having an inner lumen through which a guide wire is insertable; a metal pipe configured to be attached to an inside of the tube so as to be coaxial with the tube; a metal wire having a distal end portion welded to a region more distal than the proximal end of the pipe on an outer circumferential surface of the pipe, and a protective member formed from a resin, the protective member is fixed to a proximal end of the pipe and the protective member covers a part of an inner circumferential surface of the tube.

According to an eighth aspect of the present invention, in the guide catheter according to the seventh aspect, the proximal end of the pipe may be positioned inside the tube, and the protective member may be cured in a state in which the proximal end of the pipe is boned with the wire.

According to a ninth aspect of the present invention, in the guide catheter according to the seventh aspect, the proximal end of the pipe may be positioned inside the tube, and the protective member may be cured in a state in which the proximal end of the pipe is boned with the tube.

According to a tenth aspect of the present invention, in the guide catheter according to the ninth aspect, the protective member may be disposed on a proximal end surface of the pipe, and the protective member is disposed at an opposite side of a portion where the wire is disposed in a radial direction of the pipe.

According to an eleventh aspect of the present invention, in the guide catheter according to the seventh aspect, the proximal end of the pipe may be positioned inside the tube, and the protective member may be disposed over the whole circumference of the proximal end surface of the pipe.

According to a twelfth aspect of the present invention, in the guide catheter according to the seventh aspect, the Young's modulus of the protective member may be smaller than the Young's modulus of the pipe.

According to a thirteenth aspect of the present invention, a delivery system, includes a guide catheter having a tube into which a guidewire is insertable and a traction portion having a longitudinal axis; and a pusher catheter into which the traction portion is inserted, wherein the traction portion includes a metal pipe configured to be attached to an inside of the tube so as to be coaxial with the tube; and a metal wire having a distal end portion welded to a region more distal than a proximal end of the pipe on an outer circumferential surface of the pipe, wherein the pipe has a most proximal portion formed in a proximal end surface of the pipe, the most proximal portion is more proximal than other portions of the proximal end surface in a central axis direction of the pipe, and wherein a welding region of the wire welded to the pipe is formed on the outer circumferential surface of the pipe and a proximal end of the welding region is positioned apart from the most proximal portion of the pipe in the central axis direction of the pipe.

According to a fourteenth aspect of the present invention, in the delivery system according to the thirteenth aspect, the pipe may include an opposite portion positioned at an opposite side of the most proximal portion in a radial direction of the pipe in the proximal end surface while being positioned at a most distal end side in the proximal end surface, and the opposite portion may be positioned more proximally than the welding portion in the central axis direction of the pipe.

According to a fifteenth aspect of the present invention, in the delivery system according to the thirteenth aspect, the pipe may include an opposite portion positioned at an opposite side of the most proximal portion in a radial direction of the pipe in the proximal end surface while being positioned at a most distal end side in the proximal end surface, and the opposite portion may be positioned more distally than a proximal end of the welding region and apart from a distal end of the pipe toward the proximal end of the pipe.

According to a sixteenth aspect of the present invention, the delivery system according to the thirteenth aspect may further include a stent attached to the outer circumferential surface of the tube, wherein the pusher catheter may include a single-lumen tube and a multi-lumen tube fixed to a proximal end portion of the single-lumen tube, wherein the proximal end portion of the tube may be inserted into the single-lumen tube, wherein the wire is inserted into one of lumens of the multi-lumen tube, and wherein the stent may be configured to come in contact with a distal end of the single-lumen tube.

According to a seventeenth aspect of the present invention, in the delivery system according to the thirteenth aspect, the proximal end surface of the pipe may be inclined with the central axis of the pipe, and the pipe may include an opposite portion positioned at an opposite side of the most proximal portion in a radial direction of the pipe in the proximal end surface of the pipe while being positioned at a most distal end side in the proximal end surface of the pipe.

DETAILED DESCRIPTION OF THE INVENTION

First Embodiment

Figure 1:
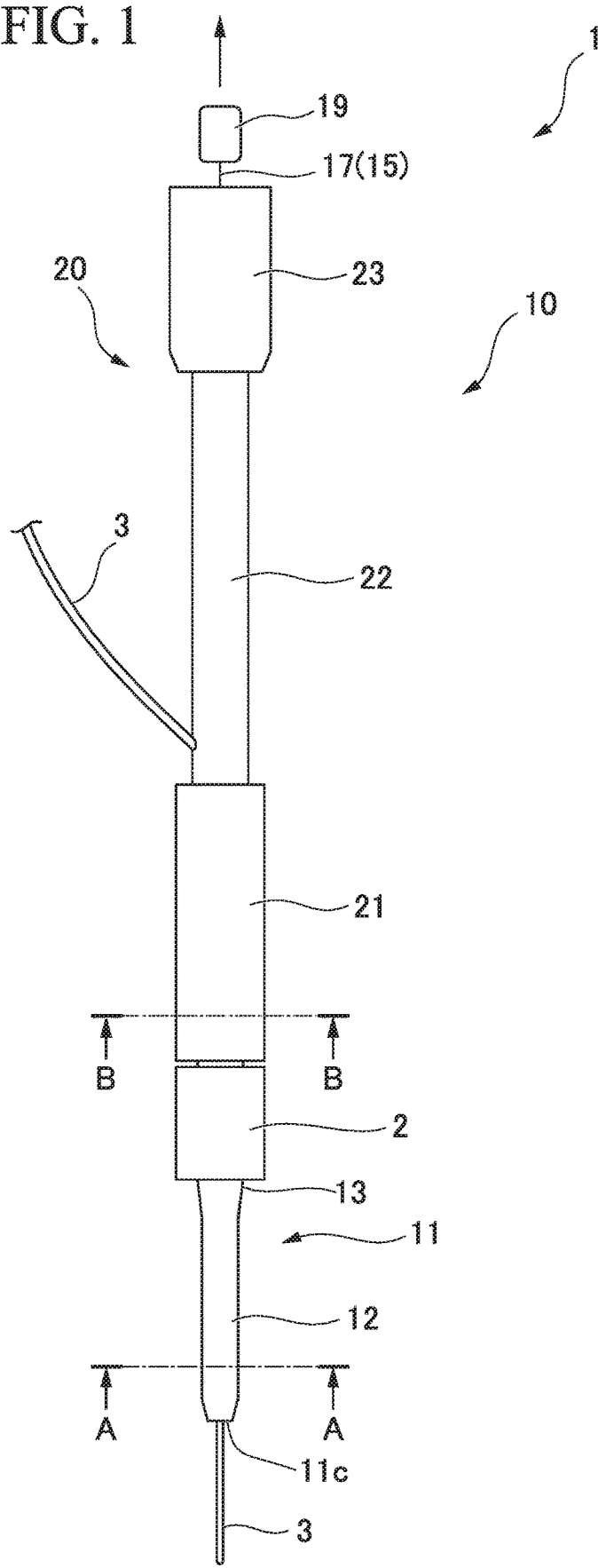
FIG. 1 is an overall view showing a delivery system having a guide catheter according to a first embodiment of the present invention.
Figure 2:
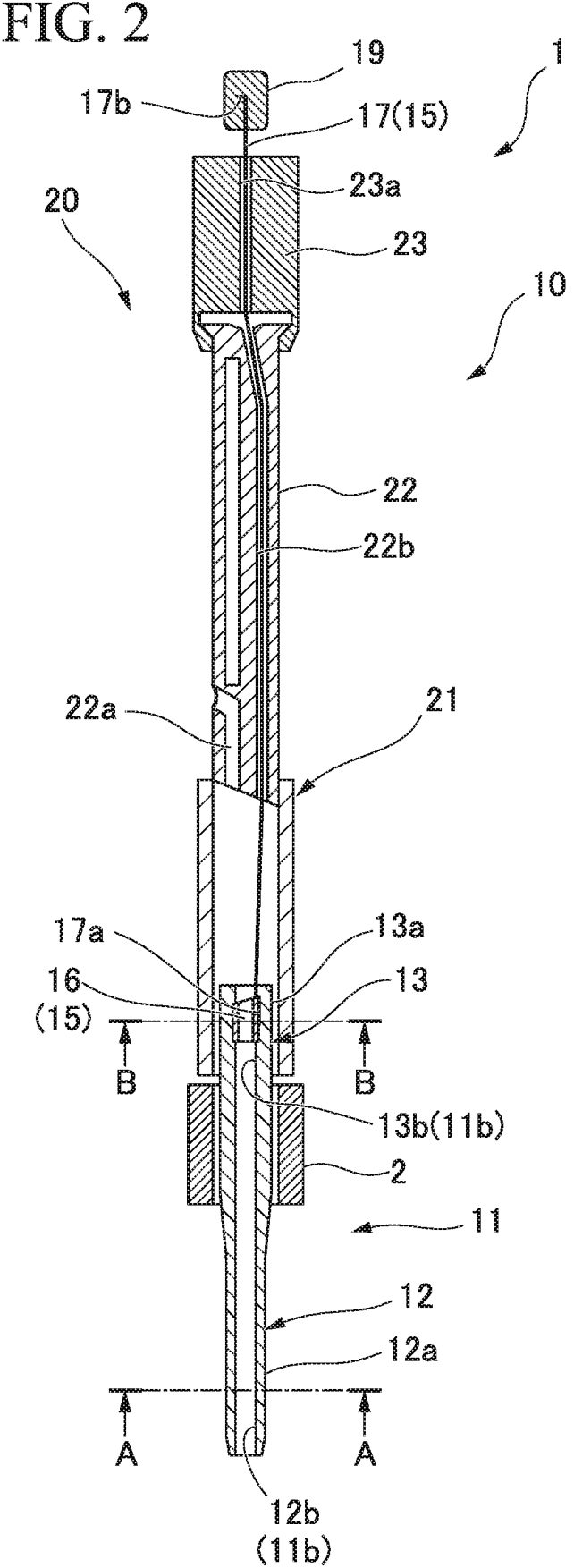
FIG. 2 is a cross-sectional view showing the delivery system in a longitudinal direction in FIG. 1.
Figure 3:
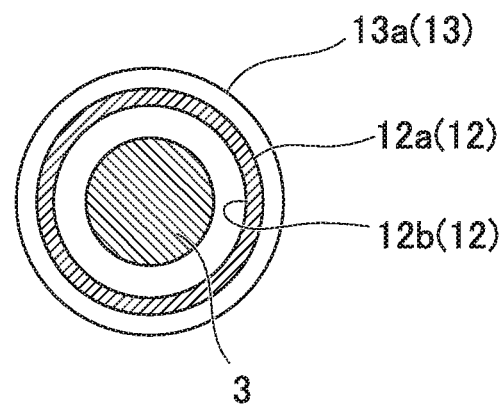
FIG. 3 is a cross-sectional view along A-A line in FIG. 1.
Figure 4:
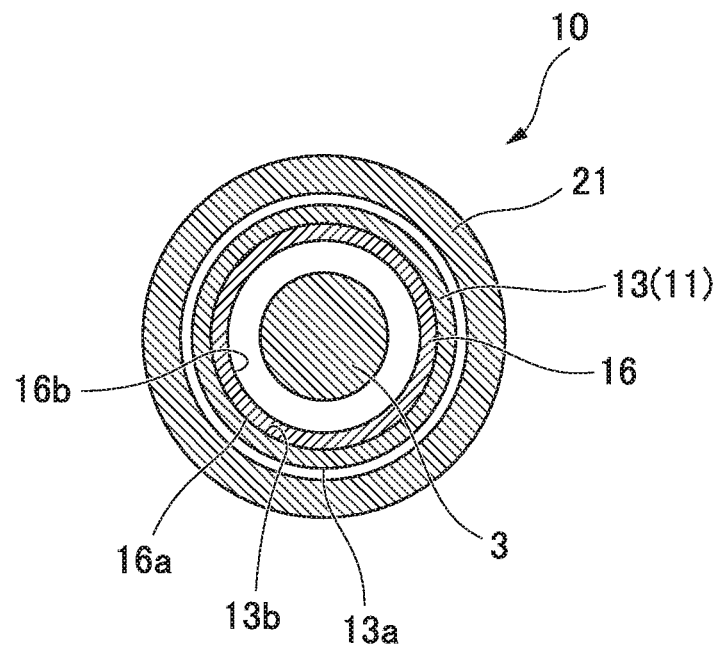
FIG. 4 is a cross-sectional view along B-B line in FIG. 1.
Figure 5:
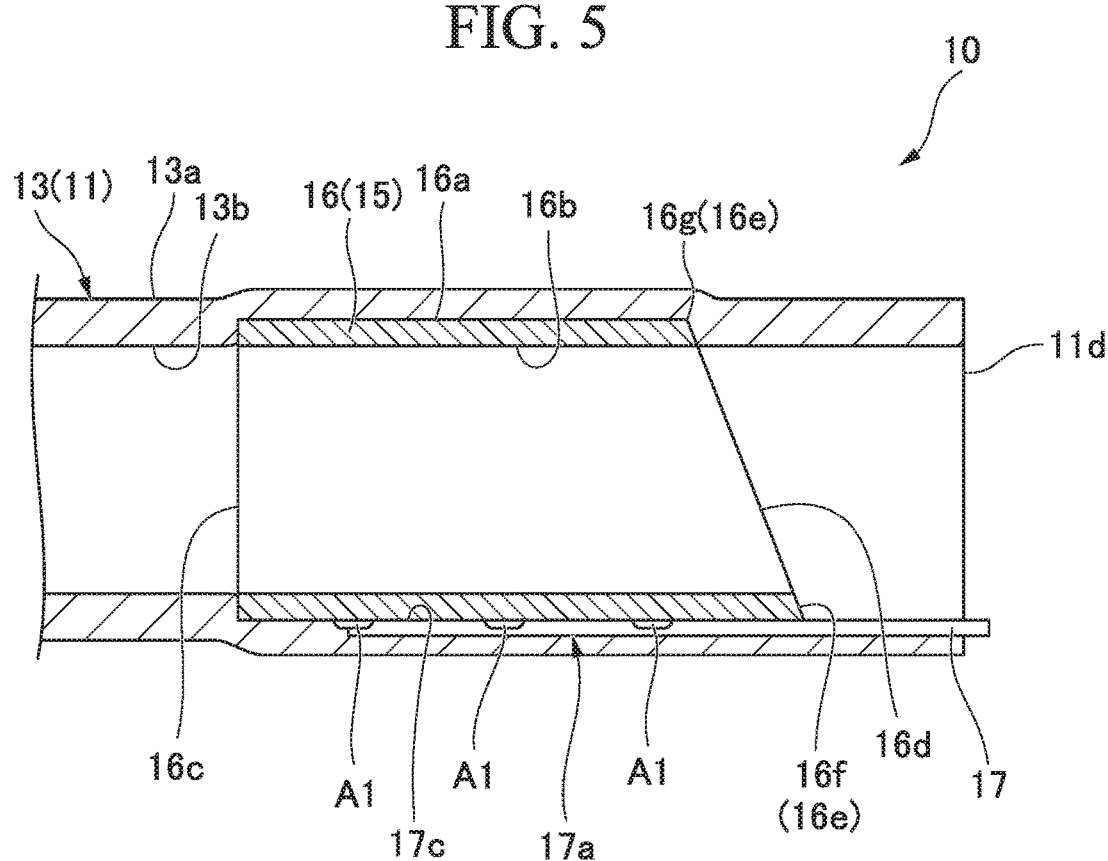
FIG. 5 is a partial cross-sectional view showing the enlarged vicinity of a pipe in the guide catheter according to the first embodiment of the present invention.
Figure 6:
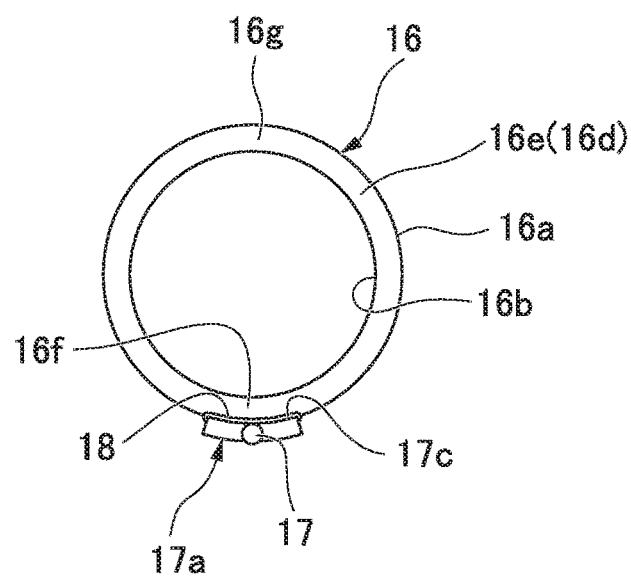
FIG. 6 is a view showing the pipe of the guide catheter according to the first embodiment of the present invention when viewed from a proximal end toward a distal end thereof.

A first embodiment of the present invention will be described. FIG. 1 is an overall view showing a delivery system having a guide catheter according to the present embodiment. FIG. 2 is a cross-sectional view showing the delivery system in a longitudinal direction in FIG. 1. FIG. 3 is a cross-sectional view along A-A line in FIG. 1. FIG. 4 is a cross-sectional view along B-B line in FIG. 1. FIG. 5 is a partial cross-sectional view showing the enlarged vicinity of a pipe in the guide catheter. FIG. 6 is a view showing the pipe of the guide catheter when viewed from a proximal end toward a distal end thereof.

A guide catheter 10 according to the present embodiment as shown in FIG. 1 is a part of a delivery system 1 configured for placing a stent 2 inside a body. The stent 2 is a tubular member formed from a metal or a resin having biocompatibility. In the present embodiment, a well-known configuration capable of being used for curing stenosis or discharging of liquid and the like may be suitably adopted as a configuration of the stent 2 used with the guide catheter 10 according to the present embodiment.

The delivery system 1 has a guide catheter 10 and the pusher catheter 2.

As shown in FIG. 1 and FIG. 2, the guide catheter 10 has a tube 11 into which a guidewire 3 is insertable and a traction portion 15 configured for moving the tube 11.

The tube 11 is a tubular member formed from a resin and has a lumen into which the guide wire 3 is insertable.

The tube 11 is flexible so as to be deformable when the tube 11 comes in contact with living tissues when the delivery system 1 is used. The tube 11 is an elastic member having a restoring force so as to be a straight-line shape in a state in which no external force is applied thereto. An inner circumferential surface 11b of the tube 11 has a circular shape in a radial cross-sectional view of the tube 11. The tube 11 has a small-diameter portion 12 positioned at a distal end side of the delivery system 1 and a large-diameter portion 13 positioned at a proximal end side of the delivery system 1.

As shown in FIG. 3, an outer circumferential surface 12a of the small-diameter portion 12 has a circular shape in a radial cross-sectional view of the tube 11. An outer diameter of the small-diameter portion 12 is smaller than the inner diameter of the stent 2.

As shown in FIG. 4, an outer circumferential surface 13a of the large-diameter portion 13 has a circular shape in a radial cross-sectional view of the tube 11. An outer diameter of the large-diameter portion 13 is substantially the same with the inner diameter of the stent 2, or the outer diameter of the large-diameter portion 13 is in a range smaller than the inner diameter of the stent 2 such that the stent 2 is slidable with respect to the large-diameter portion 13. An outer circumferential surface 16a of the pipe 16 comes in close contact with part of the inner circumferential surface 13b of the large-diameter portion 13.

The outer circumferential surface 12a of the small-diameter portion 12 and the outer circumferential surface 13a of the large-diameter portion 13 are connected with each other by a smooth curved surface such that the outer diameter of the tube changes gradually (see FIG. 2).

For example, the tube 11 according to the present embodiment is formed from a thermoplastic resin tube. In the present embodiment, the small-diameter portion 12 and the large-diameter portion 13 are formed by locally heating a thermoplastic resin tube having a constant thickness.

The connection structure of the pipe 16 and the tube 11 can also be configured by pressing the pipe 16 into a tubular resin member except for the thermoplastic resin tube.

As shown in FIG. 2 and FIG. 5, the traction portion 15 is configured for moving the tube 11 by an operation at the proximal end portion of the delivery system 1. The traction portion 15 is inserted into the inside of a pusher catheter 20.

The traction portion 15 has the pipe 16, a wire 17, and an operation portion 19.

As shown in FIG. 2, FIG. 4, FIG. 5 and FIG. 6, the pipe 16 is formed in a tubular shape so as to open at a distal end 16c and a proximal end 16d. The pipe 16 is attached to the inside of the tube 11 so as to be coaxial with the tube 11. The pipe 16 is disposed at a proximal end part of the large-diameter portion 13. The proximal end 16d of the pipe 16 is positioned inside the tube 11. In other words, the pipe 16 is covered by the large-diameter portion 13 of the tube 11.

The inner circumferential surface 11b of the tube 11 positioned at a part where the pipe 16 is positioned in the large-diameter portion 13 of the tube 11, comes in close contact with the outer circumferential surface 16a of the pipe 16. The inner diameter of the tube 11 at the part where the pipe 16 is positioned in the large-diameter portion 13 of the tube 11 is barely larger than the inner diameter of other part of the large-diameter portion 13. The outer diameter of the tube 11 at the part where the pipe 16 is positioned in the large-diameter portion 13 of the tube 11 may be barely larger than that of other part of the large-diameter portion 13. In a state in which the pipe 16 is attached to the tube 11, an inner diameter of a lumen formed by the lumen of the pipe 16 and the lumen of the tube 11 is substantially constant in the vicinity of the region where the pipe 16 is disposed.

The outer diameter of the pipe 16 is larger than the inner diameter of the tube 11 at the proximal end side and the distal end side of the pipe 16. The inner diameter of the pipe 16 is substantially the same with the inner diameter of the tube 11. The inner diameter of the pipe 16 is determined at a degree such that the guidewire 3 can be inserted into the pipe 16.

The pipe 16 has a proximal end surface 16e, a most proximal portion 16f, an opposite portion 16g. The proximal end surface 16e is configured to connect the outer circumferential surface 16a of the pipe 16 with the inner circumferential surface 16b of the pipe 16 at the proximal end 16d side of the pipe 16. The most proximal portion 16f is positioned in the proximal end surface 16e of the pipe 16 and is more proximal than other part of the proximal end surface 16e in an axial direction of the pipe 16. The opposite portion 16g is positioned in the proximal end surface 16e at an opposite side of the most proximal portion 16f in a radial direction of the pipe 16, and the opposite portion 16g is positioned more distally in the proximal end surface 16e.

The proximal end surface 16e is formed from an inclined surface with respect to a central axis of the pipe 16. An inclination angle of the proximal end surface 16e with respect to the central axis of the pipe 16 is preferable to be equal to or more than 45 degrees and less than 90 degrees.

As an example, the inclination angle of the proximal end surface 16e with respect to the central axis of the pipe 16 is 45 degrees. The part (the opposite portion 16g) being most distal in the proximal end surface 16e inclined with respect to the central axis of the pipe 16 is at a position proximal than the distal end 16c and apart from the distal end 16c of the pipe 16. A region of the pipe 16 formed in a completely tubular shape in the vicinity of the distal end 16c of the pipe 16 is configured to maintain the coaxial state of the tube 11 and the pipe 16. In the present embodiment, it is preferable that the pipe 16 is configured to have a part covering more than half of the length in the central axis direction of the pipe 16 at the distal end side thereof to be formed in a completely tubular shape.

The opposite portion 16g is connected to the outer circumferential surface 16a at an obtuse angle. In other words, at the opposite portion 16g, a dihedral angle between the outer circumferential surface 16a of the pipe 16 and the proximal end surface 16e is formed in an obtuse angle. The opposite portion 16g and the outer circumferential surface 16a of the pipe 16a may be connected by a curved surface without a clear edge.

The pipe 16 is made from a metal. A material of the pipe 16 may be suitably determined by taking the material of the wire 17 into consideration, specifically the material of the pipe 16 can be selected from well-known materials which can be bonded with the wire 17 by welding. For example, the material of the pipe 16 is the same as the material of the wire 17. A stainless steel is suitable to be used as a specific example of the material of the pipe 16. The material of the pipe 16 may be selected by taking the biocompatibility into consideration.

The wire 17 has a distal end portion 17a welded to a region which is at a distal end 16c side than the proximal end 16d of the pipe 16 on the outer circumferential surface 16a of the pipe 16. The distal end portion 17a of the wire 17 has a connection surface 17c having a shape following the shape of the outer circumferential surface 16a of the pipe 16. The connection surface 17c formed in the distal end portion 17a of the wire 17 comes in contact with the outer circumferential surface 16a of the pipe 16. The wire 17 extends toward the proximal end side in the axial direction of the pipe 16. A proximal end portion 17b of the wire 17 is connected to the operation portion 19.

The wire 17 is formed from a metal. For example, the material of the wire 17 is the same as the material of the pipe 16. The wire 17 and the pipe 16 are bonded with each other by being welded at a plurality of portions apart from each other in the axial direction of the pipe 16. The pipe 16 and the wire 17 may be continuously welded with each other in the axial direction of the pipe 16.

The wire 17 and the pipe 16 are bonded by the resistance welding. The wire 17 and the pipe 16 may be boned by other welding methods.

A welding region A1 of the wire 17 welded to the pipe 16 is at a position superimposed on the outer circumferential surface being adjacent to the most proximal portion 16f of the pipe 16, when viewed along the central axis of the pipe 16.

The proximal end 16d of the pipe 16 is not welded to the wire 17. A proximal end of the welding region A1 is at a position apart from the most proximal portion 16f at the distal end side of the most proximal portion 16f of the pipe 16, when viewed in a direction orthogonal to the central axis of the pipe 16. For example, a welding position at the most proximal side of the outer circumferential surface 16a of the pipe 16 is at a position apart from the proximal end 16d of the pipe 16 by equal to or more than 0.5 millimeters at the distal end side thereof. When viewed in a direction orthogonal to the central axis of the pipe 16, the opposite portion 16g of the pipe 16 is positioned more proximally than the welding region A1 in the central axis direction of the pipe 16.

As shown in FIG. 2, the operation portion 19 is fixed to the proximal end of the wire 17. The operation portion 19 according to the present embodiment is a member having an outer diameter larger than the outer diameter of the wire 17. An operator can easily pull the wire 17 to the hand side by pulling the operation portion 19 to the hand side.

The pusher catheter 20 has a single-lumen tube 21, a multi-lumen tube 22, and a grasping portion 23.

The single-lumen tube 21 is a tubular member into which the large-diameter portion 13 of the tube 11 of the guide catheter 10 can inserted. The single-lumen tube 21 has flexibility. A distal end surface of the single-lumen tube 21 is a surface orthogonal to a central line of the single-lumen tube 21. The distal end surface of the single-lumen tube 21 can support the stent 2 by engaging the proximal end of the stent 2. A thickness of the single-lumen tube 21 is equal to or more than a difference between an inner radius and an outer radius of the stent 2 (a thickness of the stent 2). A length of the single-lumen tube 21 in the central line direction of the single-lumen tube 21 is determined in accordance with the size of the tube 11 of the guide catheter 10, and the length is determined such that the large-diameter portion 13 of the tube 11 of the guide catheter 10 can be completely received in the inside of the single-lumen tube 21.

A material of the single-lumen tube 21 is not particularly limited.

The multi-lumen tube 22 is fixed to a proximal end portion of the single-lumen tube 21. The multi-lumen tube 22 has a guidewire lumen 22a and a wire lumen 22b. The guidewire lumen 22a is configured for inserting the guidewire 3. The wire lumen 22b is configured for inserting the wire 17 of the guide catheter 10.

The guidewire lumen 22a opens at the distal end of the multi-lumen tube 22 and the guidewire lumen 22a opens at a lateral surface of the multi-lumen tube 22 at a proximal end side from the distal end of the multi-lumen tube 22.

The wire lumen 22b opens at the distal end and the proximal end of the multi-lumen tube 22.

The grasping portion 23 is connected to the proximal end of the multi-lumen tube 22. The grasping portion 23 may be fixed to the multi-lumen tube 22 and the grasping portion 23 may not be fixed to the multi-lumen tube 22. The grasping portion 23 is formed in a substantially cylindrical shape having a diameter larger than that of the multi-lumen tube 22. An unevenness structure and the like may be formed on an outer circumferential surface of the grasping portion 23 for preventing slips.

The grasping portion 23 has a through-hole 23a formed to communicate the wire lumen 22b. The through-hole 23a formed on the grasping portion 23 is positioned on an extension line of the central line of the multi-lumen tube 22 toward the proximal end side.

The wire 17 of the guide catheter 10 is inserted into the through-hole 23a formed on the grasping portion 23. Accordingly, the wire 17 of the guide catheter 10 and the operation portion 19 extend to the outside from the through-hole 23a formed on the grasping portion 23.

Figure 7:
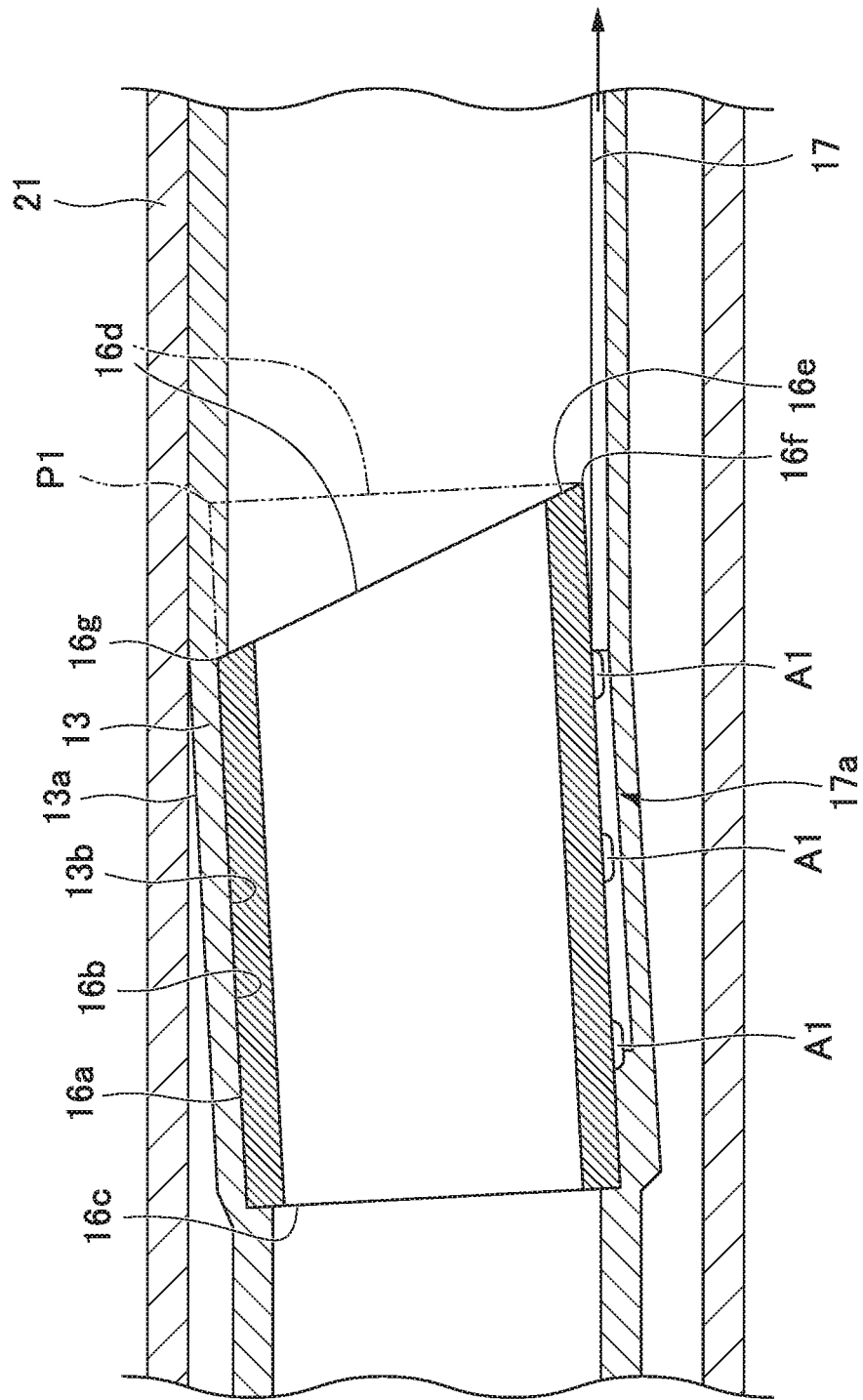
FIG. 7 is a view showing an operation of the guide catheter according to the first embodiment of the present invention.

Operations of the guide catheter 10 according to the present embodiment will be described. FIG. 7 is a view showing an operation of the guide catheter.

In a case when the stent 2 is separated from the delivery system 1 according to the present embodiment and the stent 2 is placed to a desired position, the operator of the delivery system 1 pulls the operation portion 19 to the hand side in a state of grasping the grasping portion 23.

As shown in FIG. 2 and FIG. 7, when the operator pulls the operation portion 19 for moving the tube 11 to the hand side, the pipe 16 is pulled to the hand side by the wire 17. Since the wire 17 is welded on the outer circumferential surface 16a of the pipe 16, the force applied for pulling the wire 17 to the hand side is transmitted to the outer circumferential surface 16a of the pipe 16. In the present embodiment, since the outer circumferential surface 16a of the pipe 16 comes in close contact with the inner circumferential surface 11b of the tube 11, the tube 11 is also pulled to the hand side when the pipe 16 is pulled to the hand side by the wire 17. The stent 2 is disposed on the outer circumferential surface 11a of the tube 11, further, the part in the vicinity of the proximal end 11d of the tube 11 is inserted into the single-lumen tube 21. Accordingly, friction generated between the tube 11 and the stent 2 and friction generated between the tube 11 and the single-lumen tube 21 become resistance when the tube 11 is moved to the hand side. The operator has to pull the operation portion 19 to the hand side with a force at least larger than this resistance for moving the tube 11 to the hand side.

Behaviors of the pipe 16 during the usage of the guide catheter 10 according to the present embodiment will be described in detail in accordance with FIG. 7.

In the guide catheter 10 to which the guidewire 3 is insertable, it is preferable that the inner circumferential surface 16b of the pipe 16 has a circular shape in a cross-section with less unevenness such that the guidewire 3 can be inserted into the inside of the pipe 16. Accordingly, in the present embodiment, the wire 17 is fixed on the outer circumferential surface 16a of the pipe 16.

Since the wire 17 is fixed to the outer circumferential surface 16a of the pipe 16, the pipe 16 is pulled to the proximal end side parallely with respect to the central axis of the tube 11 at a position apart from the central axis of the pipe 16. When the pipe 16 is pulled to the proximal end side by the wire 17 in a state in which the resistance with respect to the movement of the tube 11 is generated, a force for moving the pipe 16 in a direction intersecting with the central axis of the pipe 16 is generated.

When the pipe 16 is to move in the direction intersecting with the central axis of the pipe 16, the tube 11 disposed inside the single-lumen tube 21 is sandwiched by the pipe 16 and the single-lumen tube 21. When the force for moving the wire 17 to the hand side becomes larger, the force of inclining the central axis of the pipe 16 also becomes larger such that the tube 11 is sandwiched by the pipe 16 and the single-lumen tube 21 with a larger force. Accordingly, when the force for moving the wire 17 to the hand side becomes larger, the resistance occurs while moving the tube 11 to the hand side also becomes larger such that it is necessary to pull the operation portion 19 by a force larger than this resistance, and thus it is possible that the resistance further becomes larger. In this case, it is possible that the tube 11 does not move even if the operation portion 19 is pulled by a force which can make the tube 11 sandwiched by the pipe 16 and the single-lumen tube 21 to be broken.

In a case that even if an enough clearance is made between the tube 11 and the single-lumen tube 21, when the pipe 16 presses the inner circumferential surface 11b of the tube 11 so as to enlarge the inner diameter of the pipe 16 by the force of inclining the central axis of the pipe 16, it is possible that the pipe 16 breaks the tube 11 based on the amount of the pressing force.

When the tube 11 fractures, the pipe 16 and the wire 17 separate from the tube 11 such that the tube 11 cannot be moved to the hand side anymore. As a result, it is possible that the placement of the stent 2 is incomplete, or the stent 2 is not placed in an appropriate position.

An amount of the inclination of the central axis of the pipe 16 corresponding to the amount of the force of pulling the wire 17 is effected by a most proximal position in the welding region A1 between the wire 17 and the pipe 16. In other words, when the most proximal position in the welding region A1 is at the proximal end 16d of the pipe 16, it is difficult for the central axis of the pipe 16 to incline. On the other hand, it becomes easier for the central axis of the pipe 16 to incline when the most proximal position of the welding region A1 becomes the distal end 16c side of the pipe 16.

In the present embodiment, the opposite portion 16g of the pipe 16 is positioned more distally than the most proximal portion 16f of the pipe 16 in the central axis direction of the pipe 16. Accordingly, in the present embodiment, compared to a case in which the proximal end surface 16e of the pipe 16 is a surface orthogonal to the central axis of the pipe 16, when the wire 17 is pulled, a movement amount of the opposite portion 16g due to the inclination of the central axis of the pipe 16 is small. A configuration shown by the long dashed double-short dashed line and the sign P1 in FIG. 7 is a portion corresponding to the opposite portion 16g according to the present embodiment, in the case in which the proximal end surface of the pipe is a surface orthogonal to the central axis of the pipe.

It is possible to reduce the inclination of the central axis of the pipe 16 while pulling the wire 17 if the proximal end 16d of the pipe 16 and the wire 17 are welded with each other. However, in the case of welding the proximal end 16d of the pipe 16 and the wire 17, the heat for the welding is diffused by the wire 17 such that the pipe 16 and the wire 17 may not suitably bonded with each other. For example, it is possible that a bonding defect occurs because the pipe 16 and the wire 17 cannot be heated by a necessary temperature for welding, and it is possible that a strain occurs in the pipe 16 or the wire 17 is broken by heating the pipe 16 and the wire 17 by the necessary temperature for welding. Accordingly, it is difficult to weld the proximal end 16d and the wire 17 with each other.

In contrast, according to the present embodiment, even if in a state in which the proximal end 16d and the wire 17 are not welded with each other, when the wire 17 is pulled, the movement amount of the opposite portion 16g due to the inclination of the central axis of the pipe 16 is small. Accordingly, in the procedure of moving the tube 11 to the hand side, the situation in which the necessary force for moving the tube 11 becomes excessively large does not occur and it is difficult for the tube 11 to be broken.

Since the operator pulls the operation portion 19 to the hand side, the pipe 16 and the tube 11 are moved to the hand side via the wire 17 connected to the operation portion 19. The operator grasps the grasping portion 23 to hold the pusher catheter 20 such that a position of the distal end of the single-lumen tube 21 does not move. As a result, a state in which the stent 2 is disposed at the desired position is maintained, while the tube 11 of the guide catheter 10 is retracted into the single-lumen tube 21.

The stent 2 attached to the tube 11 of the guide catheter 10 contacts with the distal end of the single-lumen tube 21. Accordingly, the tube 11 of the guide catheter 10 does not move during the procedure of retracting the tube 11 of the guide catheter 10 into the single-lumen tube 21. Since the tube 11 is drawn and separated from the stent 2 by retracting the tube 11 of the guide catheter 10 into the single-lumen tube 21, the tube 11 is moved to the hand side with respect to the stent 2.

As described above, in the guide catheter 10 of the delivery system 1 according to the present embodiment, since the tube 11 is difficult to be broken when the wire 17 is pulled, it is difficult for the tube 11 and the wire 17 to be broken and separated at the connection portion of the tube 11 and the wire 17.

Second Embodiment

Figure 8:
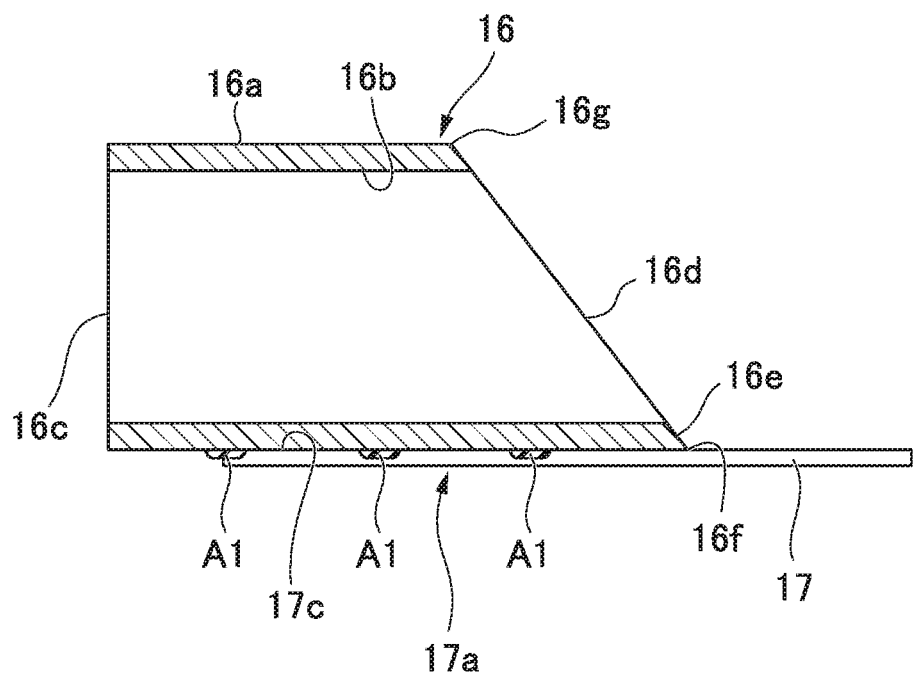
FIG. 8 is a partial cross-sectional view showing a connection structure of a pipe and a wire of a guide catheter according to a second embodiment of the present invention.

A second embodiment of the present invention will be described. FIG. 8 is a partial cross-sectional view showing a connection structure of a pipe and a wire of a guide catheter according to a second embodiment of the present invention.

As shown in FIG. 8, the present embodiment is different from the first embodiment described above in a positional relationship between the opposite portion 16g of the pipe 16 and the proximal end of the welding portion A1.

When viewed in a direction orthogonal to the central axis of the pipe 16, the opposite portion 16g is positioned at a distal end side with respect to the proximal end of the welding region A1 in the central axis direction of the pipe 16, and the opposite portion 16g is positioned apart from the distal end 16c at a proximal end side with respect to the distal end 16c of the pipe 16.

It is preferable that at least part at the distal end side of the pipe 16 of the guide catheter 10 according to the present embodiment has a completely tubular shape such that the part is continuous in the circumferential direction. A length of the region among the whole length in the central axis direction of the pipe 16 may be equal to or more than half of the whole length of the pipe 16.

Similar to the first embodiment, in the guide catheter 10 according to the present embodiment, since the tube 11 is difficult to be broken when the wire 17 is pulled, it is difficult for the tube 11 and the wire 17 to be broken and separated at the connection portion of the tube 11 and the wire 17.

According to the present embodiment, since the inclination of the central axis of the pipe 16 when the wire 17 is pulled is less than the inclination of the central axis of the pipe 16 disclosed in the first embodiment, compared to the first embodiment, it is more difficult for the tube 11 and the wire 17 to be broken and separated from each other.

Third Embodiment

Figure 9:
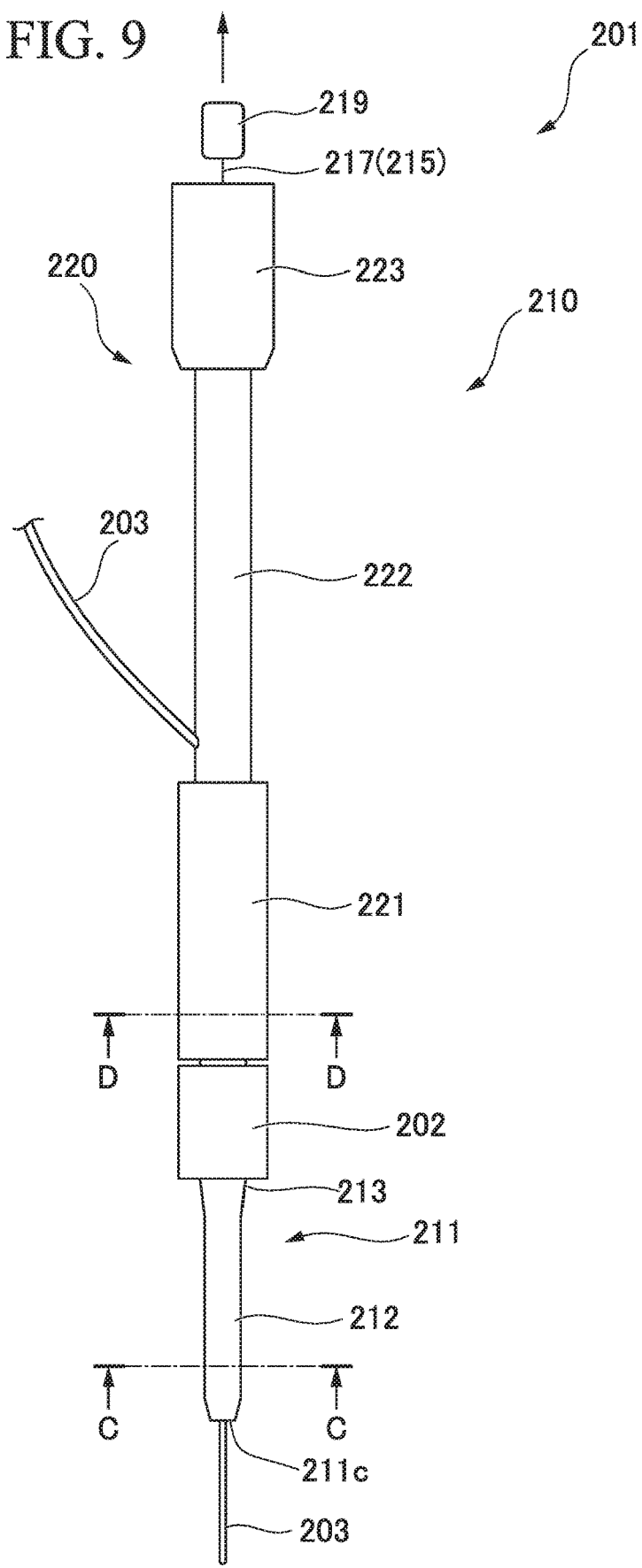
FIG. 9 is an overall view showing a delivery system having a guide catheter according to a third embodiment of the present invention.
Figure 10:
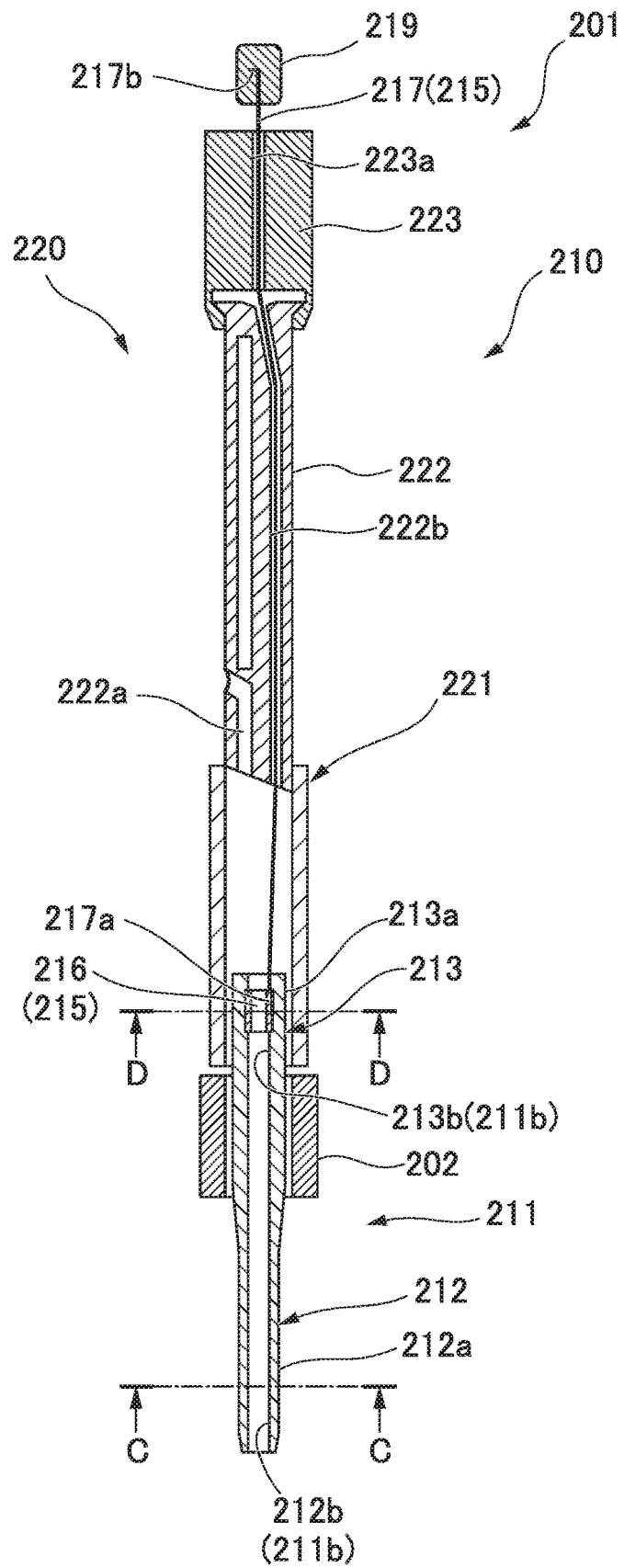
FIG. 10 is a cross-sectional view showing the delivery system in a longitudinal direction in FIG. 9.
Figure 11:
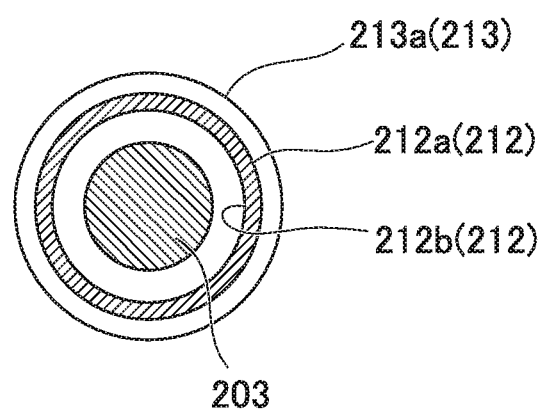
FIG. 11 is a cross-sectional view along C-C line in FIG. 9.
Figure 12:
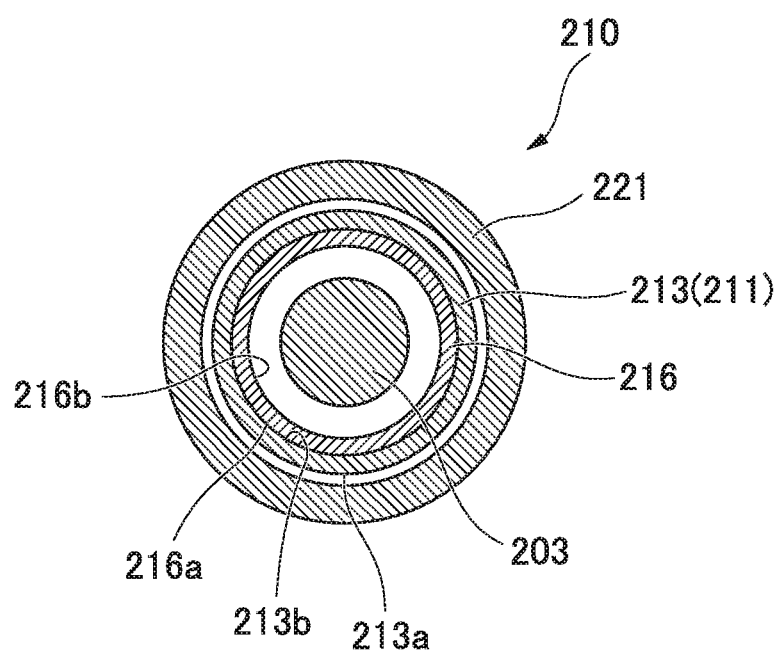
FIG. 12 is a cross-sectional view along D-D line in FIG. 9.
Figure 13:
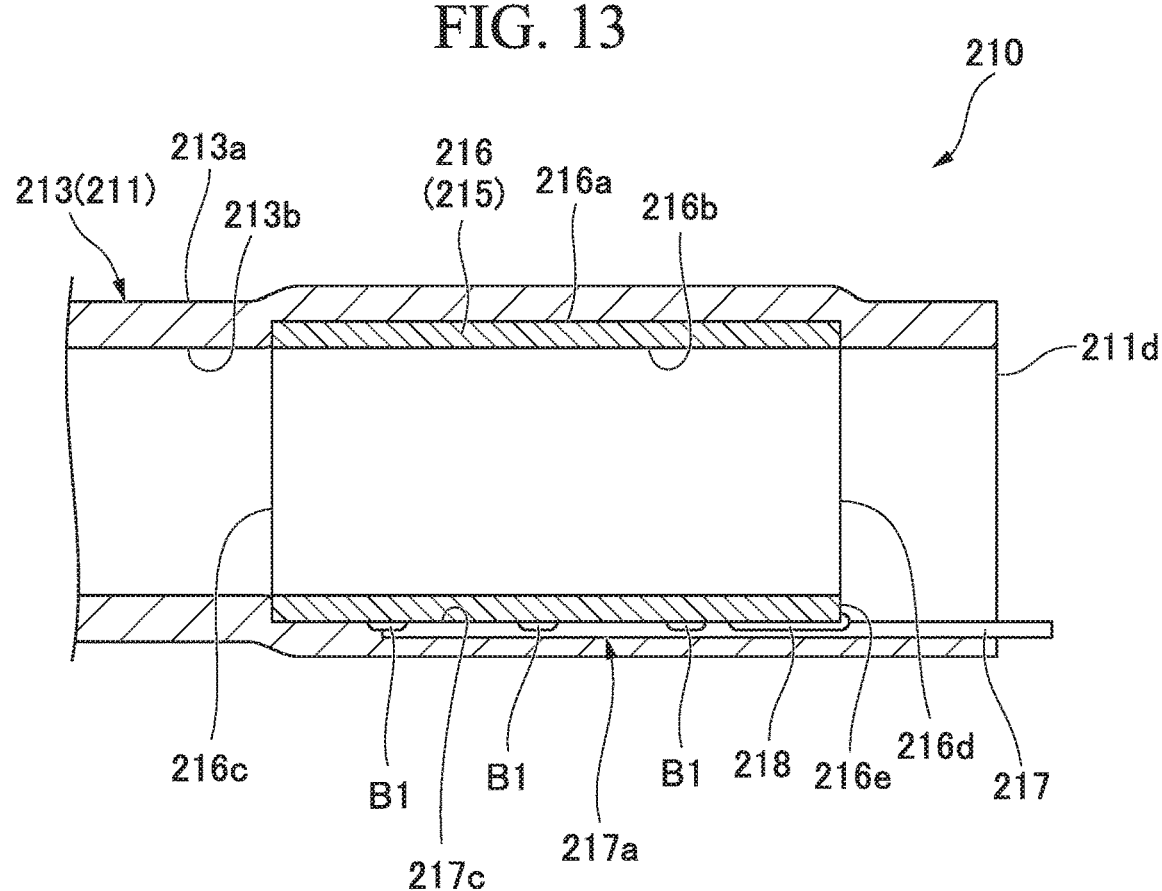
FIG. 13 is a partial cross-sectional view showing the enlarged vicinity of the pipe in the guide catheter according to the third embodiment of the present invention.
Figure 14:
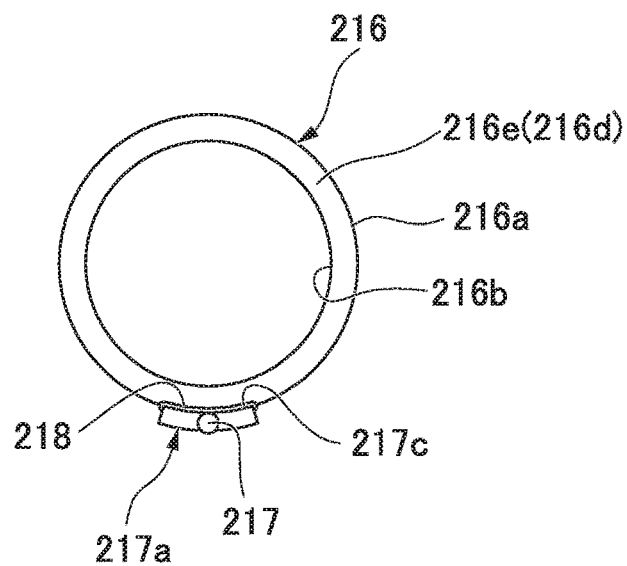
FIG. 14 is a view showing the pipe of the guide catheter according to the first embodiment of the present invention when viewed from a proximal end toward a distal end thereof.

A third embodiment of the present invention will be described. FIG. 9 is an overall view showing a delivery system having a guide catheter according to a third embodiment of the present invention. FIG. 10 is a cross-sectional view showing the delivery system in a longitudinal direction in FIG. 9. FIG. 11 is a cross-sectional view along C-C line in FIG. 9. FIG. 12 is a cross-sectional view along D-D line in FIG. 9. FIG. 13 is a partial cross-sectional view showing the enlarged vicinity of the pipe in the guide catheter according to the third embodiment of the present invention. FIG. 14 is a view showing the pipe of the guide catheter according to the first embodiment of the present invention when viewed from a proximal end toward a distal end thereof.

A guide catheter 210 according to the present embodiment as shown in FIG. 9, is a portion of a delivery system 201 for placing a stent 202 inside the body. The stent 202 is a tubular member formed from a metal or a resin having biocompatibility. In the present embodiment, a well-known configuration capable of being used for curing stenosis or discharging of liquid and the like may be suitably adopted as a configuration of the stent 202 used with the guide catheter 210 according to the present embodiment.

The delivery system 201 has a guide catheter 210 and the pusher catheter 220.

As shown in FIG. 9 and FIG. 10, the guide catheter 210 has a tube 211 into which a guidewire 203 is insertable and a traction portion 215 configured for moving the tube 211.

The tube 211 is a tubular member formed from a resin and has a lumen into which the guide wire 203 is insertable.

The tube 211 is flexible so as to be deformable when the tube 211 comes in contact with living tissues when the delivery system 201 is used. The tube 211 is an elastic member having a restoring force so as to be a straight-line shape in a state in which no external force is applied thereto. An inner circumferential surface 211b of the tube 211 has a circular shape in a radial cross-sectional view of the tube 211. The tube 211 may have a small-diameter portion 212 positioned at a distal end side of the delivery system 201 and a large-diameter portion 213 positioned at a proximal end side of the delivery system 201.

As shown in FIG. 11, an outer circumferential surface 212a of the small-diameter portion 212 has a circular shape in a radial cross-sectional view of the tube 211. An outer diameter of the small-diameter portion 212 is smaller than the inner diameter of the stent 202.

As shown in FIG. 12, an outer circumferential surface 213a of the large-diameter portion 213 has a circular shape in a radial cross-sectional view of the tube 211. An outer diameter of the large-diameter portion 213 is substantially the same with the inner diameter of the stent 202, or the outer diameter of the large-diameter portion 213 is in a range smaller than the inner diameter of the stent 202 such that the stent 2 is slidable with respect to the large-diameter portion 213. An outer circumferential surface 216a of the pipe 216 comes in close contact with part of the inner circumferential surface 213b of the large-diameter portion 213.

The outer circumferential surface 212a of the small-diameter portion 212 and the outer circumferential surface 213a of the large-diameter portion 213 are connected with each other by a smooth curved surface such that the outer diameter of the tube changes gradually (see FIG. 10).

The tube 211 according to the present embodiment is formed from a thermoplastic resin tube. In the present embodiment, the small-diameter portion 212 and the large-diameter portion 213 are formed by locally heating a thermoplastic resin tube having a constant thickness.

The connection structure of the pipe 216 and the tube 211 can also be configured by pressing the pipe 216 into a tubular resin member except for the thermoplastic resin tube.

As shown in FIG. 10 and FIG. 13, the traction portion 215 is configured for moving the tube 211 by an operation at the proximal end portion of the delivery system 201. The traction portion 215 is inserted into the inside of a pusher catheter 220.

The traction portion 215 has the pipe 216, a wire 217, and an operation portion 219.

As shown in FIG. 10, FIG. 12, FIG. 13 and FIG. 14, the pipe 216 is formed in a tubular shape so as to open at a distal end 216c and a proximal end 216d. The pipe 216 is attached to the inside of the tube 211 so as to be coaxial with the tube 211. The pipe 216 is disposed at a proximal end part of the large-diameter portion 213. The proximal end 216d of the pipe 216 is positioned inside the tube 211. The pipe 216 is covered by the large-diameter portion 213 of the tube 211.

The inner circumferential surface 211b of the tube 211 positioned at a part where the pipe 216 is positioned in the large-diameter portion 213 of the tube 211, comes in close contact with the outer circumferential surface 216a of the pipe 216. The inner diameter of the tube 211 at the part where the pipe 216 is positioned in the large-diameter portion 213 of the tube 211 is barely larger than the inner diameter of other part of the large-diameter portion 213. The outer diameter of the tube 211 at the part where the pipe 216 is positioned in the large-diameter portion 213 of the tube 211 may be barely larger than that of other part of the large-diameter portion 213. In a state in which the pipe 216 is attached to the tube 211, an inner diameter of a lumen formed by the lumen of the pipe 216 and the lumen of the tube 211 is substantially constant in the vicinity of the region where the pipe 216 is disposed.

The outer diameter of the pipe 216 is larger than the inner diameter of the tube 211 at the proximal end side and the distal end side of the pipe 216. The inner diameter of the pipe 216 is substantially the same with the inner diameter of the tube 211. The inner diameter of the pipe 216 is determined at a degree such that the guidewire 203 can be inserted into the pipe 216. A proximal end surface 216e is configured by a surface be orthogonal to the central axis of the pipe 216.

The pipe 216 is made from a metal. A material of the pipe 216 may be suitably determined by taking the material of the wire 217 into consideration, specifically the material of the pipe 216 can be selected from well-known materials which can be bonded with the wire 217 by welding. For example, the material of the pipe 216 is the same as the material of the wire 217. A stainless steel is suitable to be used as a specific example of the material of the pipe 216. The material of the pipe 216 may be selected by taking the biocompatibility into consideration.

The wire 217 has a distal end portion 217a welded to a region which is at a distal end side of the proximal end 216d of the pipe 216 on the outer circumferential surface 16a of the pipe 16. The distal end portion 217a of the wire 217 has a connection surface 217c having a shape following the shape of the outer circumferential surface 216a of the pipe 216. The connection surface 217c formed in the distal end portion 217a of the wire 217 comes in contact with the outer circumferential surface 216a of the pipe 216. The wire 217 extends toward the proximal end side in the axial direction of the pipe 216. A proximal end portion 217b of the wire 217 is connected to the operation portion 219.

The wire 217 is formed from a metal. For example, the material of the wire 217 is the same as the material of the pipe 216. The wire 217 and the pipe 216 are bonded with each other by being welded at a plurality of portions apart from each other in the axial direction of the pipe 216. The pipe 216 and the wire 217 may be continuously welded with each other in the axial direction of the pipe 216.

The wire 217 and the pipe 216 are bonded by the resistance welding. The wire 217 and the pipe 216 may be boned by other welding methods. The proximal end 216d of the pipe 216 is not welded to the wire 217. A welding position at the most proximal side of the outer circumferential surface 216a of the pipe 216 is at a position apart from the proximal end 216d of the pipe 216 by equal to or more than 0.5 millimeters at the distal end side thereof. The proximal end 216d of the pipe 216 is bonded with the wire 217 by a protective member 218 described below instead of the welding.

The protective member 218 is fixed to the proximal end 216d of the pipe 216. The protective member 218 according to the present embodiment is made from a resin. The protective member 218 according to the present embodiment is formed from a cured adhesive. The protective member 218 is cured in a state of bonding the proximal end 216d and the wire 217. Young's modulus of the protective member 218 is less than the Young's modulus of the pipe 216.

According to the present embodiment, the wire 217 is bonded on the outer circumferential surface 216a of the pipe 216 by the welding with respect to the wire 217 and the bonding using the protective member 218.

As shown in FIG. 10, the operation portion 219 is fixed to the proximal end of the wire 217. The operation portion 219 according to the present embodiment is a member having an outer diameter larger than the outer diameter of the wire 217. An operator can easily pull the wire 217 to the hand side by pulling the operation portion 219 to the hand side.

The pusher catheter 220 has a single-lumen tube 221, a multi-lumen tube 222, and a grasping portion 223.

The single-lumen tube 221 is a tubular member into which the large-diameter portion 213 of the tube 211 of the guide catheter 210 can inserted. The single-lumen tube 221 has flexibility. A distal end surface of the single-lumen tube 221 is a surface orthogonal to a central line of the single-lumen tube 221. The distal end surface of the single-lumen tube 221 can support the stent 202 by engaging the proximal end of the stent 202. A thickness of the single-lumen tube 221 is equal to or more than a difference between an inner radius and an outer radius of the stent 202 (a thickness of the stent 202). A length of the single-lumen tube 221 in the central line direction of the single-lumen tube 221 is determined in accordance with the size of the tube 211 of the guide catheter 210, and the length is determined such that the large-diameter portion 213 of the tube 211 of the guide catheter 210 can be completely received in the inside of the single-lumen tube 221.

A material of the single-lumen tube 221 is not particularly limited.

The multi-lumen tube 222 is fixed to a proximal end portion of the single-lumen tube 221. The multi-lumen tube 222 has a guidewire lumen 222a and a wire lumen 222b. The guidewire lumen 222a is configured for inserting the guidewire 203. The wire lumen 222b is configured for inserting the wire 217 of the guide catheter 210.

The guidewire lumen 222a opens at the distal end of the multi-lumen tube 222 and the guidewire lumen 222a opens at a lateral surface of the multi-lumen tube 222 at a proximal end side from the distal end of the multi-lumen tube 222.

The wire lumen 222b opens at the distal end and the proximal end of the multi-lumen tube 222.

The grasping portion 223 is connected to the proximal end of the multi-lumen tube 222. The grasping portion 223 may be fixed to the multi-lumen tube 222 and the grasping portion 223 may not be fixed to the multi-lumen tube 222. The grasping portion 223 is formed in a substantially cylindrical shape having a diameter larger than that of the multi-lumen tube 222. An unevenness structure and the like may be formed on an outer circumferential surface of the grasping portion 223 for preventing slips.

The grasping portion 223 has a through-hole 223a formed to be continuous to the wire lumen 222b. The through-hole 223a formed on the grasping portion 223 is positioned on an extension line of the central line of the multi-lumen tube 222 toward the proximal end side.

The wire 217 of the guide catheter 210 is inserted into the through-hole 223a formed on the grasping portion 223. Accordingly, the wire 217 of the guide catheter 210 and the operation portion 219 extend to the outside from the through-hole 223a formed on the grasping portion 223.

Figure 15:
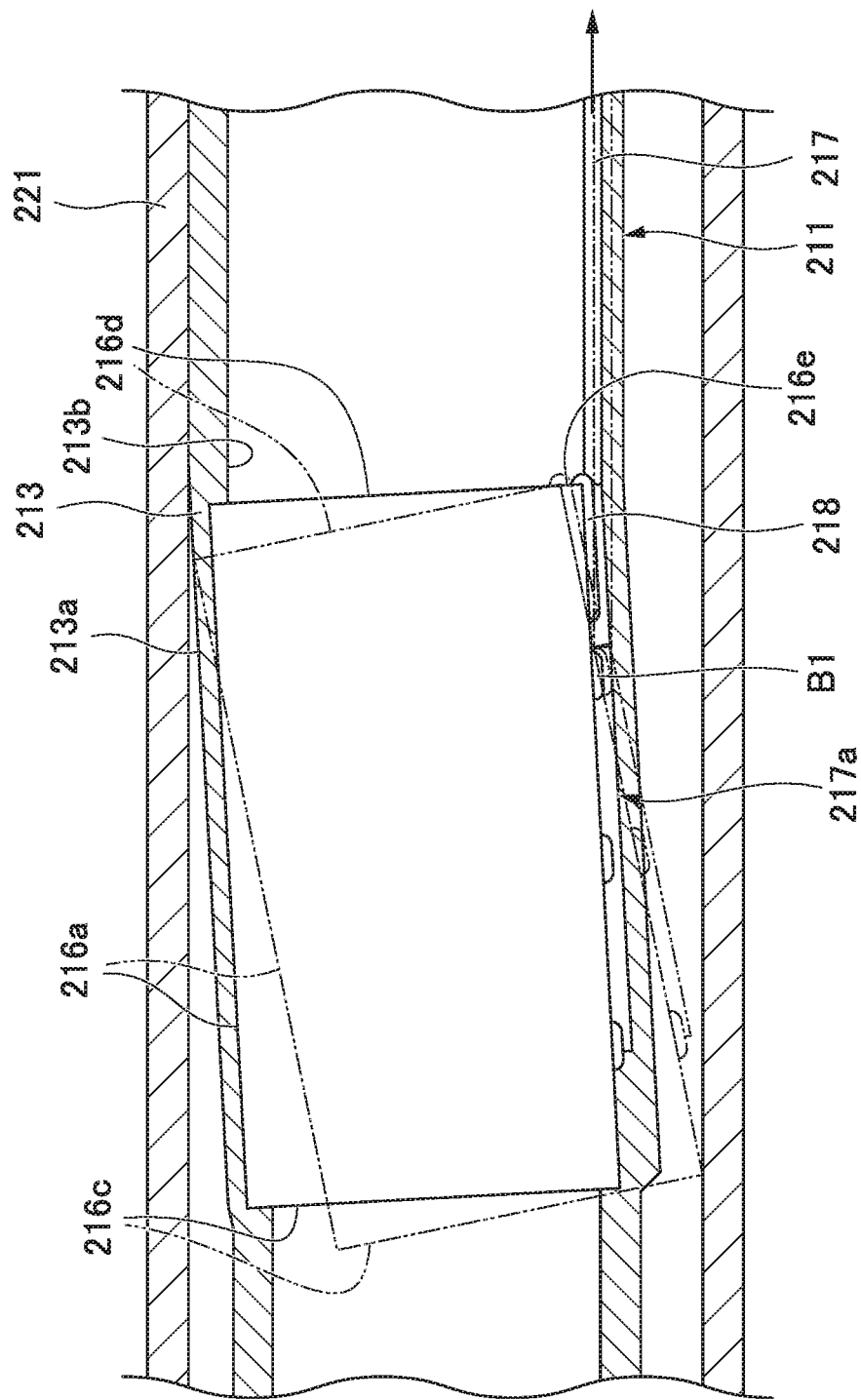
FIG. 15 is a view showing an operation of the guide catheter according to the third embodiment of the present invention.

Operations of the guide catheter 210 according to the present embodiment will be described. FIG. 15 is a view showing an operation of the guide catheter.

In a case when the stent 202 is separated from the delivery system 201 according to the present embodiment and the stent 202 is placed to a desired position, the operator of the delivery system 201 pulls the operation portion 219 to the hand side in a state of grasping the grasping portion 23.

As shown in FIG. 10 and FIG. 15, when the operator pulls the operation portion 219 for moving the tube 211 to the hand side, the pipe 216 is pulled to the hand side by the wire 217. Since the wire 217 is welded on the outer circumferential surface 216a of the pipe 216, the force applied for pulling the wire 217 to the hand side is transmitted to the outer circumferential surface 216a of the pipe 216. In the present embodiment, since the outer circumferential surface 216a of the pipe 216 comes in close contact with the inner circumferential surface 211b of the tube 211, the tube 211 is also pulled to the hand side when the pipe 216 is pulled to the hand side by the wire 217. The stent 202 is disposed on the outer circumferential surface 211a of the tube 211, further, the part in the vicinity of the proximal end 211d of the tube 211 is inserted into the single-lumen tube 221. Accordingly, friction generated between the tube 211 and the stent 202 and friction generated between the tube 211 and the single-lumen tube 221 become resistance when the tube 211 is moved to the hand side. The operator has to pull the operation portion 219 to the hand side with a force at least larger than this resistance for moving the tube 211 to the hand side.

Differences between the behaviors of the pipe 16 during the usage of the guide catheter 210 having the protective member 218 according to the present embodiment and the behaviors of the pipe 16 during the usage of the catheter without the protective member 218 will be described in accordance with FIG. 15.

In the guide catheter 210 to which the guidewire 203 is insertable, it is preferable that the inner circumferential surface 216b of the pipe 216 has a circular shape in a cross-section with less unevenness such that the guidewire 203 can be inserted into the inside of the pipe 216. Accordingly, in the present embodiment, the wire 217 is fixed on the outer circumferential surface 216a of the pipe 216.

Since the wire 217 is fixed to the outer circumferential surface 216a of the pipe 216, the pipe 216 is pulled to the proximal end side parallely with respect to the central axis of the tube 211 at a position apart from the central axis of the pipe 216. When the pipe 216 is pulled to the proximal end side by the wire 217 in a state in which the resistance with respect to the movement of the tube 211 is generated, a force for moving the pipe 216 in a direction intersecting with the central axis of the pipe 216 is generated.

When the pipe 216 is to move in the direction intersecting with the central axis of the pipe 216, the tube 211 disposed inside the single-lumen tube 221 is sandwiched by the pipe 216 and the single-lumen tube 221. When the force for moving the wire 217 to the hand side becomes larger, the force of inclining the central axis of the pipe 216 also becomes larger such that the tube 211 is sandwiched by the pipe 216 and the single-lumen tube 221 with a larger force. Accordingly, when the force for moving the wire 217 to the hand side becomes larger, the resistance occurs while moving the tube 211 to the hand side also becomes larger such that it is necessary to pull the operation portion 219 by a force larger than this resistance, and thus it is possible that the resistance further becomes larger. In this case, it is possible that the tube 211 does not move even if the operation portion 219 is pulled by a force which can make the tube 211 sandwiched by the pipe 216 and the single-lumen tube 221 to be broken.

In a case that even if an enough clearance is made between the tube 211 and the single-lumen tube 221, when the pipe 216 presses the inner circumferential surface 211b of the tube 211 so as to enlarge the inner diameter of the pipe 216 by the force of inclining the central axis of the pipe 216, it is possible that the pipe 216 breaks the tube 211 based on the amount of the pressing force.

When the tube 211 fractures, the pipe 216 and the wire 217 separate from the tube 211 such that the tube 211 cannot be moved to the hand side anymore. As a result, it is possible that the placement of the stent 202 is incomplete, or the stent 202 is not placed in an appropriate position.

An amount of the inclination of the central axis of the pipe 216 corresponding to the amount of the force of pulling the wire 217 is effected by a most proximal position in the welding region A1 between the wire 217 and the pipe 216. For example, in a case in which the protective member 218 is not provided in the pipe 216, the proximal end of the welding region described above is a proximal end of the welding region B1. In a case in which the protective member is provided in the pipe 216, the proximal end of the welding region described above is a proximal end of the protective member 218 (that is, the position of the proximal end surface 216e of the pipe 216).

When the most proximal position in the welding region is at the proximal end 216d of the pipe 216, it is difficult for the central axis of the pipe 216 to incline. On the other hand, it becomes easier for the central axis of the pipe 216 to incline when the most proximal position of the welding region becomes the distal end 216c side of the pipe 216.

According to the present embodiment, in order to fix the wire 217 formed from a metal on the outer circumferential surface 216a of the pipe 216 formed from a metal, both of the fixation by the welding at the welding region B1 and the fixation by using the protective member 21 are used. The protective member 218 is configured to connect the proximal end 216d of the pipe 216 and the wire 217 at the proximal end 216d of the pipe 216. Accordingly, in the present embodiment, an inclination amount of the central axis of the pipe 216 when the wire 217 is pulled is smaller than that according to the case in which the proximal end 216d of the pipe 216 and the wire 217 are not connected. In other words, the protective member 218 according to the present embodiment is configured to protect the inner circumferential surface 211b of the tube 211 for preventing the tube 211 from breaking by suppressing the inclination of the central axis of the pipe 216 to a minimum value.

In a case of welding the proximal end 216d of the pipe 216 and the wire 217 instead of using the protective member 218, the heat for the welding is diffused by the wire 217 such that the pipe 216 and the wire 217 may not suitably bonded with each other. For example, it is possible that a bonding defect occurs because the pipe 216 and the wire 217 cannot be heated by a necessary temperature for welding, and it is possible that a strain occurs in the pipe 216 or the wire 217 is broken by heating the pipe 216 and the wire 217 by the necessary temperature for welding. Accordingly, it is difficult to weld the proximal end 216d and the wire 217 with each other.

In contrast, according to the present embodiment, the protective member 218 is formed from a resin and the protective member 218 is configured to connect the pipe 216 and the wire 217. More specifically, the wire 217 can be fixed to the proximal end 216d of the pipe 216 by coating a resin fluid to the pipe 216 and the wire 217 and then curing the resin fluid. Accordingly, there is no possibility that the strain of the pipe 216 is generated by heating and the wire 217 is broken, and the bonding of the proximal end 216d and the wire 217 is easy. It is possible that a bonding strength of the pipe 216 and the wire 217 by using the protective member 218 is weaker than the bonding strength of the pipe 216 and the wire 217 by the welding. However, according to the present embodiment, since the pipe 216 and the wire 217 are welded in a region at the distal end side of the protective member 218, an enough high overall bonding strength can be achieved.

Since the proximal end 216d and the wire 217 are bonded by the protective member 218, the inclination of the central axis of the pipe 216 when the wire 217 is pulled is suppressed to the minimum, thus even the proximal end 216d of the pipe 216 and the wire 217 are not welded, the proximal end 216d of the pipe 216 and the wire 217 do not separate. Accordingly, in the procedure of moving the tube 211 to the hand side, the situation in which the force necessary for moving the tube 211 becomes excessively large will not occur and it is difficult for the tube 211 to be broken.

Since the operator pulls the operation portion 219 to the hand side, the pipe 216 and the tube 211 are moved to the hand side via the wire 217 connected to the operation portion 219. The operator grasps the grasping portion 223 to hold the pusher catheter 220 such that a position of the distal end of the single-lumen tube 221 does not move. As a result, a state in which the stent 202 is disposed at the desired position is maintained, while the tube 211 of the guide catheter 210 is retracted into the single-lumen tube 221.

The stent 202 attached to the tube 211 of the guide catheter 210 contacts with the distal end of the single-lumen tube 221. Accordingly, the tube 211 of the guide catheter 210 does not move during the procedure of retracting the tube 211 of the guide catheter 210 into the single-lumen tube 221. Since the tube 211 is drawn and separated from the stent 202 by retracting the tube 211 of the guide catheter 210 into the single-lumen tube 221, the tube 211 is moved to the hand side with respect to the stent 202.

As described above, in the guide catheter 210 of the delivery system 201 according to the present embodiment, since the tube 211 is difficult to be broken when the wire 217 is pulled, it is difficult for the tube 211 and the wire 217 to be broken and separated at the connection portion of the tube 211 and the wire 217.

Fourth Embodiment

Figure 16:
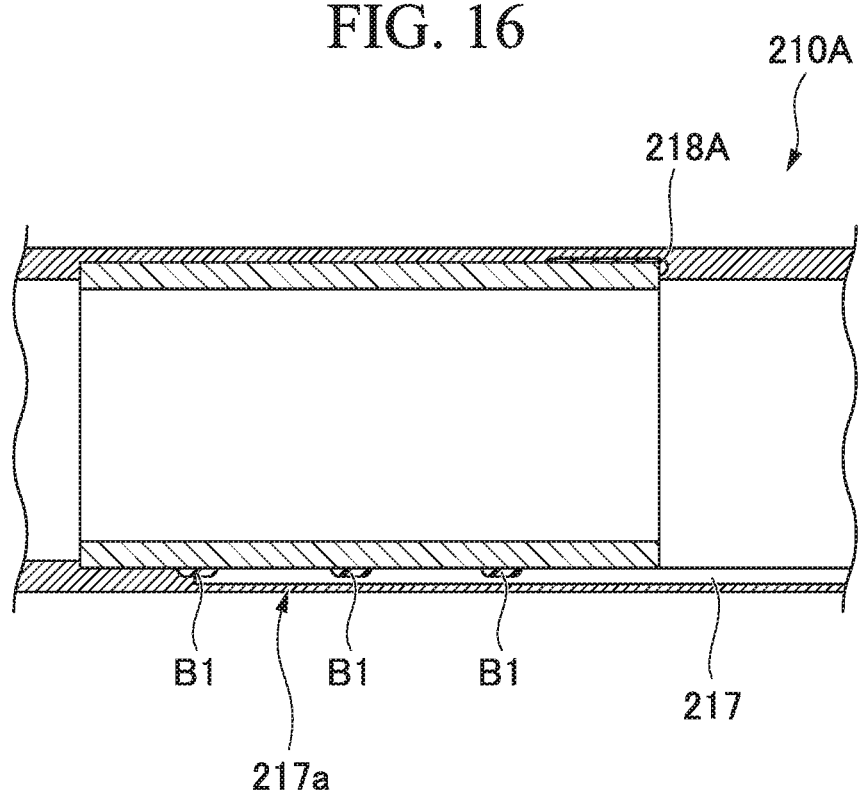
FIG. 16 is a partial cross-sectional view showing a connection structure of a pipe and a wire of a guide catheter according to a fourth embodiment of the present invention.

A fourth embodiment of the present invention will be described. FIG. 16 is a partial cross-sectional view showing a connection structure of a pipe and a wire of a guide catheter according to a fourth embodiment of the present invention.

As shown in FIG. 16, a guide catheter 210A according to the present embodiment has a protective member 218A different from the protective member 218 according to the third embodiment.

The guide catheter 210A according to the present embodiment is different from the third embodiment in that the protective member 218A is cured in a state of bonding the proximal end 216d and the tube 211.

According to the present embodiment, the proximal end 216d of the pipe 216 and the wire 217 are not bonded by the protective member 218A. The protective member 218A is disposed on the proximal end surface 216e of the pipe 216 at an opposite side with respect to the position where the wire 217 is disposed in a radial direction of the pipe 216.

During the manufacturing process of the guide catheter 210A, the protective member 218A according to the present embodiment is configured to be bonded to both of the pipe 216 and the tube 211 by being coated on the proximal end 216d of the pipe 216 in a fluid state before curing, and then disposing the pipe 216 inside the tube 211 before the fluid is cured.

According to the present embodiment, the pipe 216 and the tube 211 are bonded by the protective member 218A. Accordingly, in the case when the wire 217 is pulled to the hand side, the pipe 216 does not move with respect to the tube 211 and the pipe 216 and the tube 211 are integrally moved to the hand side. Accordingly, the protective member 218A according to the present embodiment is configured to bond the proximal end 216d of the pipe 216 and the inner circumferential surface 211b of the tube 211 such that it is possible to suppress the possibility to the minimum that the tube 211 is broken due to a relative movement of the pipe 216 with respect to the tube 211 resulting that the proximal end 216d of the pipe 216 bites into the inner circumferential surface 211b of the tube 211.

Similar to the third embodiment, in the guide catheter 210A in the delivery system 201 according to the present embodiment, it is difficult for the tube 211 to be broken when the wire 217 is pulled such that it is difficult for the tube 211 and the wire 217 to be broken and separated from each other at the connection portion of the tube 211 and the wire 217.

The protective member 218A disposed at the proximal end 216d of the pipe 216 according to the present embodiment is configured to cover a corner formed by the outer circumferential surface 216a and the proximal end surface 216e of the pipe 216. Accordingly, the corner is prevent from directly contacting with the inner circumferential surface 211b of the tube 211. Further, the Young's modulus of the protective member 218A is less than the Young's modulus of the pipe 216 such that a pressing force by the pipe 216 toward the inner circumferential surface 211b of the tube 211 via the protective member 218A is smaller than a pressing force generated in a case in which the pipe 216 directly presses the inner circumferential surface 211b of the tube 211 without the protective member 218A. Accordingly, the protective member 218 of the guide catheter 210A according to the present embodiment can protect the inner circumferential surface 211b of the tube 211.

As another example of the guide catheter 210A according to the present embodiment, the guide catheter 210A may have both of the protective member 218 disclosed in the third embodiment and the protective member 218A disclosed in the fourth embodiment. In this case, the protective members 218, 218A are configured to bond the proximal end 216d of the pipe 216 and the inner circumferential surface 211b of the tube 211 while bonding the proximal end 216d of the pipe 216 and the wire 217.

The protective members 218, 218A may be provided on the whole circumference of the proximal end surface 216e of the pipe 216. In this case, the same effect as that of the third embodiment can be achieved by bonding the proximal end surface 216e and the wire 217 by the protective members 218, 218A.

Embodiments of the present invention have been described above with reference to the drawings, but specific structures of the invention are not limited to the embodiments and may include various modifications without departing from the scope of the invention. Furthermore, it is clear that the configuration according to each embodiment can be suitably combined to be adopted. The invention is not limited to the above-mentioned embodiments and is limited only by the accompanying claims.

What is claimed is:
1. A guide catheter comprising:
a tube formed from a resin and having an inner lumen through which a guide wire is insertable;
a metal pipe configured to be attached to an inside of the tube so as to be coaxial with the tube; and
a metal wire having a distal end portion welded to a region more distal than a proximal end of the pipe on an outer circumferential surface of the pipe, wherein:
the pipe includes (i) a proximal end that has a proximal end surface, the proximal end surface being defined by a two-dimensional plane when viewed in an axial cross-section, the plane being inclined relative to a longitudinal axis of the pipe, such that a lower apex of the cross-sectional shape of the pipe is located proximal along a direction of the longitudinal axis of the pipe relative to an upper apex of the cross-sectional shape of the pipe in the plane, and (ii) an opposite portion positioned at the upper apex of the cross-sectional shape of the pipe, the opposite portion being located at a distal end side in the proximal end surface of the pipe, such that the opposite portion and the outer circumferential surface of the pipe are connected at an obtuse angle or with a curved surface, and
a welding region of the wire welded to the pipe is formed on the outer circumferential surface of the pipe, the welding region including a plurality of welds attaching the wire to the pipe, which are spaced apart from each other in the longitudinal axis direction of the pipe, and a proximal end of the welding region is positioned apart from the lower apex of the cross-sectional shape of the pipe in the direction of the longitudinal axis of the pipe, whereby movement of the wire causes the pipe to incline to generate friction with the tube and correspondingly move the tube proximally as the wire is pulled proximally.
2. The guide catheter according to claim 1, wherein:
the opposite portion is positioned more proximally than the welding portion of the pipe.
3. The guide catheter according to claim 1, wherein:
the opposite portion is positioned more distally than a proximal end of the welding region and apart from a distal end of the pipe toward the proximal end of the pipe.

4. The guide catheter according to claim 1, wherein:
the proximal end surface of the pipe is inclined with respect to the longitudinal axis of the pipe.

\* \* \* \* \*